United States Patent [19]

Bissery et al.

[11] Patent Number: 6,146,663
[45] Date of Patent: *Nov. 14, 2000

[54] STABILIZED NANOPARTICLES WHICH MAY BE FILTERED UNDER STERILE CONDITIONS

[75] Inventors: Marie-Christine Bissery, Vitry sur Seine; Michel Laborie; Joël Vacus, both of Paris; Thierry Verrecchia, Arcueil, all of France

[73] Assignee: Rhone-Poulenc Rorer S.A., Antony, France

[*] Notice: This patent issued on a continued prosecution application filed under 37 CFR 1.53(d), and is subject to the twenty year patent term provisions of 35 U.S.C. 154(a)(2).

[21] Appl. No.: 08/929,226

[22] Filed: Sep. 9, 1997

Related U.S. Application Data

[63] Continuation of application No. 08/467,652, Jun. 6, 1995, abandoned.

[30] Foreign Application Priority Data

Jun. 22, 1994 [FR] France ................... 94 07628

[51] Int. Cl.$^7$ ............... A61K 9/16; A61K 9/10
[52] U.S. Cl. .......... 424/489; 424/490; 424/496; 424/497; 424/498; 424/501; 424/502
[58] Field of Search ............ 424/489–502; 514/937–943

[56] References Cited

U.S. PATENT DOCUMENTS

| | | | |
|---|---|---|---|
| 4,711,895 | 12/1987 | Hazato | 514/530 |
| 5,025,004 | 6/1991 | Wu | 514/165 |
| 5,469,854 | 11/1995 | Unger | 424/450 |
| 5,500,224 | 3/1996 | Vranckx | 424/451 |

FOREIGN PATENT DOCUMENTS

| | | |
|---|---|---|
| 0 167 825 | 1/1986 | European Pat. Off. . |
| 0 520 888 | 12/1992 | European Pat. Off. . |
| 0 520 889 | 12/1992 | European Pat. Off. . |
| WO 90/15593 | 12/1990 | WIPO . |
| WO 91/15193 | 10/1991 | WIPO . |

OTHER PUBLICATIONS

J. Cont. Release, vol. 30, Apr. 1994, p. 83–94, Schwartz et al., "Solid Lipid Nanoparticles (SLN) for Controlled Drug Delivery . . . ".

Eric Allémann et al., "Drug–Loaded Nanoparticles—Preparation Methods and Drug Targeting Issues," Eur. J. Pharm. Biopharm., 39(5), 173–191 (1993).

Grant & Hack's Dictionary p. 145, 1969.

*Primary Examiner*—Gollamudi S. Kishore
*Attorney, Agent, or Firm*—Finnegan, Henderson, Farabow, Garrett & Dunner, L.L.P.

[57] ABSTRACT

This invention relates to stabilized nanoparticles which may be filtered under sterile conditions, comprising at least one hydrophobic, water-insoluble and non-water-dispersible polymer or copolymer (and optionally an active principle) which is emulsified in an aqueous solution or suspension comprising a phospholipid and a bile salt.

20 Claims, No Drawings

STABILIZED NANOPARTICLES WHICH MAY BE FILTERED UNDER STERILE CONDITIONS

This application is a continuation of application Ser. No. 08/467,652, filed Jun. 6, 1995 now abandoned.

FIELD OF THE INVENTION

The present invention relates to very small nanoparticles which have, besides the advantage of being able to circulate in the bloodstream without any problems of size in the capillaries, the advantages of being stabilized, of being able to be filtered in a sterile manner, and of being able to be freeze-dried.

BACKGROUND OF THE INVENTION

European Patent Applications EP-A-523,183, EP-A-520,888 and EP-A-520,889 describe small spherical particles having the advantage of being injectable. However, the nanoparticles thus prepared have mean diameters of the order of 50 to 500 nm and may not be sterilized by sterilizing filtration without a considerable loss in yield, and/or may not be freeze-dried owing to insufficient stability.

In Eur. J. Pharm. Biopharm., 39(5), 173–191 (1993) the authors examined the technologies currently available in the field of nanoparticles intended for the pharmaceutical industry. It is stated on page 182 that the sterile filtration of nanoparticle suspensions has never been described.

According to the present invention, it is possible to prepare particles, of which 95% have a mean diameter less than 100 nm, and more preferably whose mean diameter is between 20 and 75 nm and which may thus be subjected to sterile filtration on a 0.22 $\mu$m filter without loss of yield. The particles are, moreover, more stable than those obtainable according to the prior art and may be freeze-dried without any agglomeration of the particles occurring.

DESCRIPTION OF THE INVENTION

The present invention accordingly provides stabilised nanoparticles comprising a hydrophobic, water-insoluble and non-water-dispersible polymer or copolymer emulsified in an aqueous solution or dispersion which comprises a phospholipid and a bile salt.

According to the invention, an active principle may be introduces into the nanoparticles with the polymer or the copolymer.

The phospholipid may be, for example, a natural, synthetic or semi-synthetic phospholipid; preferably a lecithin (e.g. phosphatidylcholine), such as purified egg or soya lecithin (e.g. LECITHIN E100®, LECITIN E80® or a PHOSPHOLIPON ®, such as PHOSPHOLIPON 90®), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, distearoylphosphatidylcholine or phosphatidic acid, or a mixture of two or more thereof.

The bile salt may be, for example, a salt derived from cholic acid, preferably a cholate, taurocholate, glycocholate, deoxycholate, chenodeoxycholate, glycodeoxycholate, taurodeoxycholate, taurochenodeoxycholate or dehydrocholate, or a derivative of said salt, or a mixture of two or more thereof. The sodium salt is preferably used.

The hydrophobic, water-insoluble and non-water-dispersible polymer or copolymer may be, for example, a biocompatible or biodegradable polymer, for example lactic or glycolic acid polymer or a copolymer thereof, or a polylactic/poly(ethylene oxide) (or poly(propylene oxide)) copolymer preferably having a molecular weight between 1000 and 200,000, a polyhydroxy-butyric acid polymer, a polylactone of a fatty acid containing at least 12 carbon atoms or a polyanhydride.

The nanoparticles according to the invention may further comprise a hydrophobic active principle. The active principle may be, for example, a pharmaceutical active principle intended for human or veterinary medicine. It may also be a substance intended for the cosmetics or agri-foods industry or a diagnostic agent.

By way of example, active principles of interest to the pharmaceutical industry may be chosen, without any limitation being implied, from anti-rheumatic agents, non-steroidal anti-inflammatory agents, analgesics, antitussive agents, psychotropes, steroids, barbiturates, antimicrobial agents, anti-allergic agents, anti-asthmatic agents, anti-spasmodic agents and anti-secretary agents, cerebral vasodilators and cardiovascular agents, cerebral protecting agents and hepatic protecting agents, therapeutic agents of the gastrointestinal tract, anticancer agents or anti-viral agents, vitamins, contraceptives and vaccines.

According to the invention, the nanoparticles may be obtained by the solvent evaporation technique, starting with an aqueous solution or dispersion comprising a phospholipid and a bile salt, adding to the aqueous solution or dispersion an immiscible organic phase comprising a hydrophobic, water-insoluble and non-water-dispersible polymer or copolymer and, where appropriate, an active principle. The mixture is pre-emulsified and then homogenized and the organic solvent is evaporated to give an aqueous suspension of very small nanoparticles.

The implementation of this process is described in greater detail in the Examples.

The solvent used in the immiscible organic phase is preferably a volatile solvent and is preferably a good solvent for the polymer system used. For example, an ester, preferably ethyl acetate, a chlorinated solvent, e.g. dichloromethane or chloroform, or a ketone, such as methyl ethyl ketone, may be used.

In general, the active principle preferably constitutes approximately 25% by weight relative to the amount of polymer introduced. However, this amount may vary; it may be lower or may even be up to 50% by weight relative to the amount of polymer or copolymer introduced.

The immiscible organic phase is preferably formulated such that the active principle an the polymer or the copolymer represent from 0.1 to 7% by weight of the solution.

The aqueous phase is preferably an aqueous solution or dispersion of a phospholipid and a bile salt comprising these constituents in a respective molar proportion of about 1/1. However, this proportion may vary such that the molar ration of the phospholipids to the bile salts is from 0.1 to 1.

The aqueous phase is preferably formulated such that the phospholipid and the bile salt represent in total from 0.2 to 2% by weight of the solution.

The relative amounts of the organic phase and the aqueous phase are preferably chosen such that the organic phase represents 20 to 60% by volume relative to the aqueous phase.

The nanoparticles thus obtained may be filtered without giving rise to problems of blocking and in good yields. The filtration is preferably carried out by cascade filtrations on filters of decreasing porosity, with a last filtration on a 0.22 $\mu$m filter.

After filtration, the suspension obtained is preferably freeze-dried in the presence of one or more cryoprotective agents. The cryoprotective agent preferably constitutes approximately 5% (weight/volume) of the suspension subjected to the freeze-drying.

A solution intended for freeze-drying may comprise certain additives such as nonionic compounds, for example a cryoprotective agent or an agent intended to adjust the isotonicity of the final solution to be injected. These agents may, for example, be chosen from sugars (e.g. glucose, mannitol, sorbitol, or sucrose), polymers [e.g. dextran (such as dextran 1500 or dextran 40,000), an injectable polyvinylpyrrolidone or polyethylene glycol], amino acids (e.g. glycine), or any other agent which may exert a similar function. It may also contain one (or more) preserving agent(s). Where appropriate, the lyophilisate may be taken up in water at the time of use for injectable preparations. It is understood that such operations do not modify the size of the particles.

The nanoparticles according to the invention are particularly advantageous on account of their stability. This stability makes it possible in particular to obtain a lyophilisate of good quality whose dissolution or dispersion, during use, is improved and for which the reconstituted suspension contains particles of diameter close to that of the initial nanoparticles.

The nanoparticles according to the invention may be used for the preparation of sterile compositions intended for the pharmaceutical or veterinary fields, for the cosmetics or agri-foods field or for diagnostic agents.

This technique is particularly advantageous since it opens the route to the industrial-scale preparation of stabilized and decontaminated nanoparticle suspensions, optionally comprising active principles, which was not possible hitherto.

In addition, the stabilized nanoparticles according to the invention have a considerable advantage in the case of certain active principles such as, for example, anticancer agents of the taxoid family. Indeed, they allow the activity of the product to increase when compared with conventional formulations.

The product of Example 6 studied via the i.v. route in mice on melanoma B16 proved to be twice as active in nanoparticle composition form when compared with a conventional formulation in a polysorbate 80/ethanol/5% dextrose in water (5/5/90 by volume) mixture.

The present invention also relates to pharmaceutical compositions comprising nanoparticles according to the invention, optionally in combination with one or more compatible and pharmaceutically acceptable excipients or adjuvants. These compositions are preferably injectable compositions.

Administration via the parenteral route includes intravenous, intraperitoneal, intramuscular and subcutaneous administration. Intraperitoneal and intravenous administration are preferred.

The compositions according to the invention preferably comprise at least 0.01% of therapeutically active ingredient. The amount of active ingredient in a composition is such that an acceptable dosage may be prescribed. The compositions are preferably prepared in such a way that a single dose comprises about 0.01 to 1000 mg of active ingredient for administration via the parenteral route.

The dose for a human patient is generally between 0.01 and 200 mg/kg. For intravenous administration, the dose is generally between 0.1 and 50 mg/kg, preferably between 0.1 and 8 mg/kg. It will be understood that, in order to choose the most appropriate dose, it is necessary to take into account the route of administration, the weight, general state of health and age of the patient and all other factors which may influence the effectiveness of the treatment.

The Examples which follow, given without any limitation being implied, illustrate the present invention.

EXAMPLE 1

4.0 g of poly (d,l-lactic acid) of molecular weight 2000 D and 1.0 g of (3aS,4S,7aS)-7,7-diphenyl-4-(2-methoxyphenyl)-2-[(S)-2-(2-methoxyphenyl)propionyl] perhydro-4-isoindolol are dissolved in a volume of 100 ml of ethyl acetate heated on a water bath to a temperature of 45° C. (solution A). 1.25 g of sodium cholate and 1.75 g of LECITHIN E80® are dispersed with ULTRA-TURRAX® stirring in a volume of 500 ml of water for an injectable preparation (solution B).

Solution A is pre-emulsified in solution B for 1 minute with the ULTRA-TURRAX®. The pre-emulsion is then introduced into an homogenizer of type MICROFLUIDIZER 110 T®, where it undergoes 20 successive passages at a working pressure of 6 bar and a cooling temperature of 0° C.

A volume of 610 ml of the emulsion is introduced into a 2-litre round-bottomed flask. The ethyl acetate is evaporated off using a rotary evaporator, under vacuum+microbleed, at a temperature of 30° C. for about 45 minutes. A volume of 450 ml of nanoparticle suspension is recovered and is completed to 500 ml with water for an injectable preparation.

At a pressure of 0.5 bar of nitrogen, the suspension is filtered successively on 4 membranes of MILLIPORE® cellulose esters, 45 mm in diameter and of referenced decreasing porosities: RAWP 1.2 $\mu$m, AAWP 0.8 $\mu$m, HAWP 0.45 $\mu$m and GSWP 0.22 $\mu$m.

The sterile filtered suspension is divided into 2 parts. One is freeze-dried in the presence of 5% weight/volume of glucose, the other is freeze-dried in the presence of 5% weight/volume of sucrose.

The mean diameter of the particles measured by light scattering on a BROOKHAVEN® machine, before freeze-drying and after the lyophilisate is taken up in the same volume of water for injectable preparations (in both cases), is about 70 nm.

The production yield, expressed as the ratio of the final concentration of (3aS,4S,7aS)-7,7-diphenyl-4-(2-methoxyphenyl)-2-[(S)-2-(2-methoxyphenyl)propionyl] perhydro-4-isoindolol after filtration to the initial theoretical concentration (2 mg/ml), is 95%.

The optical density at 405 nm of the suspension before and after the last filtration on the 0.22 $\mu$m filter is 2.20 and 2.10 respectively.

The concentration of (3aS,4S,7aS)-7,7-diphenyl-4-(2-methoxyphenyl)-2-[(S)-2-(2-methoxyphenyl)propionyl] perhydro-4-isoindolol before and after the last filtration on the 0.22 $\mu$m filter remains unchanged.

(3aS,4S,7aS)-7,7-Diphenyl-4-(2-methoxyphenyl)-2-[(S)-2-(2-methoxyphenyl)propionyl]perhydro-4-isoindolol may be prepared as described in International patent application WO 93/21155.

EXAMPLE 2

By working as above in Example 1, but starting with 4.0 g of a diblock copolymer consisting of the combination of a poly(d,l-lactic acid) of molecular weight 30 kD and a polyethylene glycol of molecular weight 2 kD (PLA-PEG) and 1.0 g of (3aS,4S,7aS)-7,7-diphenyl-4-(2-methoxyphenyl)-2-[(S)-2-(2-methoxyphenyl)propionyl] perhydro-4-isoindolol, a nanoparticle suspension is obtained.

At a pressure of 0.5 bar of nitrogen, the suspension is filtered successively on 4 membranes of MILLIPORE® cellulose esters, 45 mm in diameter and of referenced decreasing porosities: RAWP 1.2 μm, AAWP 0.8 μm, HAWP 0.45 μm and GSWP 0.22 μm.

The sterile filtered suspension is freeze-dried in the presence of 5% w/v of glucose.

The mean diameter of the particles measured by light scattering on a BROOKHAVEN® machine, before freeze-drying and after the lyophilisate is taken up in the same volume of water for injectable preparations is about 75 nm.

The production yield, expressed as the ratio of the final concentration of (3aS,4S,7aS)-7,7-diphenyl-4-(2-methoxyphenyl)-2-[(S)-2-(2-methoxyphenyl)propionyl] perhydro-4-isoindolol after filtration to the initial theoretical concentration (2 mg/ml), is 98%.

The optical density at 405 nm of the suspension before and after the last filtration on the 0.22 μm filter is 2.7 and 2.6 respectively.

The concentration of (3aS,4S,7aS)-7,7-diphenyl-4-(2-methoxyphenyl)-2-[(S)-2-(2-methoxyphenyl)propionyl] perhydro-4-isoindolol before and after the last filtration on the 0.22 μm filter remains unchanged.

EXAMPLE 3

160 mg of poly(d,l-lactic acid) of molecular weight 70,000 D and 40 mg of (3aS,4S,7aS)-7,7-diphenyl-4-(2-methoxyphenyl)-2-[(S)-2-(2-methoxyphenyl)propionyl] perhydro-4-isoindolol are dissolved in a volume of 4 ml of ethyl acetate heated on a water bath to a temperature of 45° C. (solution A). 100 mg of sodium cholate and 70 mg of LECITHIN E80® are dispersed with ULTRA-TURRAX® stirring in a volume of 20 ml of water for an injectable preparation (solution B).

Solution A is pre-emulsified in solution B for 1 minute with the ULTRA-TURRAX®. The pre-emulsion is then introduced into an homogenizer of type MICROFLUIDIZER 110 S®, where it undergoes 3 minutes of continuous recycling at a working pressure of 6 bar and a cooling temperature of 0° C.

A volume of 30 ml of the emulsion is introduced into a 200 ml round-bottomed flask. The ethyl acetate is evaporated off using a rotary evaporator, under vacuum+ microbleed, at a temperature of 30° C. for about 45 minutes. A volume of 19 ml of nanoparticle suspension is recovered and is completed to 20 ml with water for an injectable preparation.

The suspension is filtered successively on 2 membranes of MILLIPORE® cellulose esters, 25 mm in diameter and of referenced decreasing porosities: HAWP 1.2 μm and SLGS 0.22 μm.

The sterile filtered suspension is divided into 2 parts. One is freeze-dried in the presence of 5% weight/volume of glucose, the other is freeze-dried in the presence of 5% weight/volume of sucrose.

The mean diameter of the particles measured by light scattering on a BROOKHAVEN® machine, before freeze-drying and after the lyophilisate is taken up in the same volume of water for injectable preparations (in both cases), is about 60 nm.

The optical density at 405 nm of the suspension before and after the final filtration on the 0.22 μm filter is 1.29 and 1.14 respectively.

The concentration of (3aS,4S,7aS)-7,7-diphenyl-4-(2-methoxyphenyl)-2-[(S)-2-(2-methoxyphenyl)propionyl] perhydro-4-isoindolol before and after the last filtration on the 0.22 μm filter remains unchanged.

EXAMPLE 4

160 mg of poly(d,l-lactic acid) of molecular weight 70,000 D and 40 mg of (3aS,4S,7aS)-7,7-diphenyl-4-(2-methoxyphenyl)-2-[(S)-2-(2-methoxyphenyl)propionyl] perhydro-4-isoindolol are dissolved in a volume of 4 ml of ethyl acetate heated on a water bath to a temperature of 45° C. (solution A). 50 mg of sodium cholate and 70 mg of LECITHIN E80® are dispersed with ULTRA-TURRAX® stirring in a volume of 20 ml of water for an injectable preparation (solution B).

Solution A is pre-emulsified in solution B for 1 minute with the Ultra-turrax®. The pre-emulsion is then introduced into an homogenizer of type MICROFLUIDIZER 110 S®, where it undergoes 3 minutes of continuous recycling at a working pressure of 6 bar and a cooling temperature of 0° C.

A volume of 30 ml of the emulsion is introduced into a 200 ml round-bottomed flask. The ethyl acetate is evaporated off using a rotary evaporator, under vacuum+ microbleed, at a temperature of 30° C. for about 45 minutes. A volume of 19 ml of nanoparticle suspension is recovered and is completed to 20 ml with water for an injectable preparation.

The suspension is filtered successively on 2 membranes of MILLIPORE® cellulose esters, 25 mm in diameter and of referenced decreasing porosities: HAWP 1.2 μm and SLGS 0.22 μm.

The sterile filtered suspension is divided into 2 parts. One is freeze-dried in the presence of 5% weight/volume of glucose, the other is freeze-dried in the presence of 5% weight/volume of sucrose.

The mean diameter of the particles measured by light scattering on a Brookhaven® machine, before freeze-drying and after the lyophilisate is taken up in the same volume of water for injectable preparations (in both cases), is about 70 nm.

The optical density at 405 nm of the suspension before and after the last filtration on the 0.22 μm filter is 1.88 and 1.80 respectively.

The concentration of (3aS,4S,7aS)-7,7-diphenyl-4-(2-methoxyphenyl)-2-[(S)-2-(2-methoxyphenyl)propionyl] perhydro-4-isoindolol before and after the final filtration on the 0.22 μm filter remains unchanged.

EXAMPLE 5

400 mg of a diblock copolymer consisting of the combination of a poly(d,l-lactic acid) of molecular weight 30 kD and a polyethylene glycol of molecular weight 2 kD (PLA-PEG) and 100 mg of (3aS,4S,7aS)-7,7-diphenyl-4-(2-methoxyphenyl)-2-[(S)-2-(2-methoxyphenyl)propionyl] perhydro-4-isoindolol are dissolved in a volume of 10 ml of ethyl acetate heated on a water bath to a temperature of 45° C. (solution A). 125 mg of sodium cholate and 175 mg of LECITHIN E80® are dispersed with ULTRA-TURRAX® stirring in a volume of 50 ml of water for an injectable preparation (solution B).

Solution A is pre-emulsified in solution B for 1 minute with the ULTRA-TURRAX®. The pre-emulsion is then introduced into an homogenizer of type MICROFLUID-IZER 110 S®, where it undergoes 10 minutes of continuous recycling at a working pressure of 6 bar and a cooling temperature of 0° C.

A volume of 60 ml of the emulsion is introduced into a 200 ml round-bottomed flask. The ethyl acetate is evaporated off using a rotary evaporator, under vacuum+ microbleed, at a temperature of 30° C. for about 45 minutes. A volume of 45 ml of nanoparticle suspension is recovered and is completed to 50 ml with water for an injectable preparation.

The suspension is filtered successively on 2 membranes of MILLIPORE® cellulose esters, 25 mm in diameter and of referenced decreasing porosities: HAWP 1.2 µm and SLGS 0.22 µm.

The sterile filtered suspension is freeze-dried in the presence of 5% w/v of glucose.

The mean diameter of the particles measured by light scattering on a BROOKHAVEN® machine, before freeze-drying and after the lyophilisate is taken up in the same volume of water for injectable preparations, is about 60 nm.

The optical density at 405 nm of the suspension before and after the last filtration on the 0.22 µm filter is 0.87 and 0.81 respectively.

The concentration of (3aS,4S,7aS)-7,7-diphenyl-4-(2-methoxyphenyl)-2-[(S)-2-(2-methoxyphenyl)propionyl] perhydro-4-isoindolol before and after the last filtration on the 0.22 µm filter remains unchanged.

EXAMPLE 6

300 mg (15 mg/ml theoretical) of a diblock copolymer consisting of the combination of a poly(d,l-lactic acid) of molecular weight 30 kD and a polyethylene glycol of molecular weight 2 kD (PLA-PEG) and 100 mg (5 mg/ml theoretical) of 4α,10β-diacetoxy-2α-benzoyloxy-5β,20-epoxy-1β-hydroxy-7β,8β-methylene-9-oxo-19-nor-11-taxen-13α-yl (2R, 3S)-3-tert-butoxycarbonylamino-2-hydroxy-3-phenylpropionate are dissolved in 8 ml of ethyl acetate (solution A). 70 mg of lecithin E80 and 50 mg of sodium cholate are dispersed in 20 ml of 5% w/v glucose solution (solution B). Solution A is emulsified in solution /b with the ULTRA-TURRAX® and the pre-emulsion is then introduced into an homogenizer of type MICROFLUID-IZER 110 S® for 3 minutes at 10° C. The volume of emulsion recovered is about 30 ml (30 g). The ethyl acetate is removed using a rotary evaporator under reduced pressure (100 mm of mercury) to a suspension volume of about 17 ml (17 g). The suspension is filtered on two filters in series of decreasing porosity (1.2 µm Minisart NML®+0.22 µm SLGS®). Two identical suspensions were prepared under the same conditions and combined in the same flask. The filtered suspension is sterile.

The mean diameter of the particles measured by light scattering on a BROOKHAVEN® machine is about 75 nm.

The optical density at 405 nm of the suspension before and after the final filtration on the 0.22 µm filter is 7.2.

The production yield, expressed as the ratio of the final concentration of 4α,10β-diacetoxy-2α-benzoyloxy-5β,20-epoxy-1β-hydroxy-7β,8β-methylene-9-oxo-19-nor-11-taxen-13α-yl (2R, 3S)-3-tert-butoxycarbonylamino-2-hydroxy-3-phenylpropionate after filtration to the initial theoretical concentration (5 mg/ml), is 94%.

The concentration of PLA-PEG (calculated relative to the yield of 4α,10β-diacetoxy-2α-benzoyloxy-5β,20-epoxy-1β-hydroxy-7β,8β-methylene-9-oxo-19-nor-11-taxen-13α-yl (2R, 3S)-3-tert-butoxycarbonylamino-2-hydroxy-3-phenylpropionate) is 14.1 mg/ml.

4α,10β-Diacetoxy-2α-benzoyloxy-5β,20-epoxy-1β-hydroxy-7β,8β-methylene-9-oxo-19-nor-11-taxen-13α-yl (2R, 3S)-3-tert-butoxycarbonylamino-2-hydroxy-3-phenylpropionate may be prepared as described in International patent application WO 94/13654.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Stabilized nanoparticles which may be filtered under sterile conditions through a filter having a porosity of 220 nm, comprising a hydrophobic, water-insoluble polymer and copolymer suspended in an aqueous solution or dispersion comprising a phospholipid and a bile salt, wherein said hydrophobic, water-insoluble polymer or copolymer cannot be dispersed in water without the aid of a dispersing agent.

2. Stabilized nanoparticles according to claim 1, further comprising an active principle.

3. Stabilized nanoparticles according to claim 1, wherein said hydrophobic, water-insoluble polymer and copolymer is a biocompatible or biodegradable polymer.

4. Stabilized nanoparticles according to claim 1, wherein 95% of said nanoparticles have a mean diameter of less than 100 nm.

5. Stabilized nanoparticles according to claim 1, of sterile quality, wherein said nanoparticles have been sterilized by filtration.

6. Stabilized nanoparticles according to claim 5, wherein the sterilizing filtration has been carried out in a cascade, on filters of decreasing porosity.

7. Stabilized nanoparticles according to claim 1, wherein said nanoparticles have been freeze-dried.

8. Stabilized nanoparticles according to claim 1, wherein said nanoparticles have undergone sterilizing filtration, freeze-drying and redispersing.

9. A process for the preparation of stabilized nanoparticles, said process comprising:
preparing an aqueous solution or dispersion comprising a phospholipid and a bile salt,
adding to the aqueous solution of dispersion an immiscible organic phase including, in an organic solvent, a hydrophobic, water-insoluble polymer or copolymer and, optionally, an active principle, to obtain a mixture, wherein said hydrophobic, water-insoluble polymer or copolymer cannot be dispersed without the aid of a dispersing agent,
pre-emulsifying and the homogenizing the mixture,
evaporating the organic solvent from said mixture to obtain a suspension, and
the filtering and optionally freeze-drying the suspension obtained.

10. A process for the preparation of a composition which may be sterilized by sterilizing filtration through a filter having a porosity of 220 nm, said process comprising including in said composition stabilized nanoparticles according to claim 1.

11. A pharmaceutical composition comprising stabilized nanoparticles according to claim 1, optionally in combination with at least one compatible and pharmaceutically acceptable excipient or adjuvant.

12. An emulsion comprising a hydrophobic, water-insoluble polymer or copolymer emulsified in an aqueous solution or dispersion comprising a phospholipid and a bile salt, wherein said hydrophobic, water-insoluble polymer or copolymer cannot be dispersed without the aid of a dispersing agent.

13. An emulsion according to claim 12, further comprising an active principle.

14. An emulsion according to claim 12, wherein said hydrophobic, water-insoluble polymer and copolymer is a biocompatible or biodegradable polymer.

15. A process for the preparation of an emulsion, said process comprising:

preparing an aqueous solution or dispersion comprising a phospholipid and a bile salt, adding to the aqueous solution or dispersion an immiscible organic phase including, in an organic solvent, a hydrophobic, water-insoluble polymer or copolymer to obtain a mixture, wherein said hydrophobic, water-insoluble polymer or copolymer cannot be dispersed without the aid of a dispersing agent, and pre-emulsifying and then homogenizing the mixture.

16. A process according to claim 15, wherein an active principle is added to said aqueous solution or dispersion.

17. A process according to claim 16, wherein said hydrophobic, water-insoluble polymer or copolymer is a biocompatible or biodegradable polymer.

18. A process according to claim 9, wherein 95% of said stabilized nanoparticles have a mean diameter less than 100 nm.

19. A process according to claim 9, further comprising sterilizing said stabilized nanoparticles by filtration.

20. A process according to claim 19, wherein said filtration has been carried out in a cascade, on filters of decreasing porosity.

* * * * *

UNITED STATES PATENT AND TRADEMARK OFFICE
CERTIFICATE OF CORRECTION

PATENT NO.   : 6,146,663
DATED        : November 14, 2000
INVENTOR(S)  : Marie-Christine Bissery et al.

It is certified that error appears in the above-identified patent and that said Letters Patent is hereby corrected as shown below:

Claim 1, col. 8, line 18, "polymer and" should read --polymer or--.
Claim 3, col. 8, line 26, "polymer and" should read --polymer or--.
Claim 9, col. 8, line 47, "solution of dispersion" should read --solution or dispersion--.
Claim 9, col. 8, line 54, "the homogenizing" should read --then homogenizing--.
Claim 9, col. 8, line 57, "the filtering" should read --then filtering--.

Signed and Sealed this

Twenty-ninth Day of May, 2001

*Attest:*

NICHOLAS P. GODICI

*Attesting Officer*      *Acting Director of the United States Patent and Trademark Office*